United States Patent
Schmid

(10) Patent No.: US 6,616,446 B1
(45) Date of Patent: Sep. 9, 2003

(54) WORKING DEVICE FOR DRILLING, CUTTING AND SCREWDRIVER INSTRUMENTS USED FOR MEDICAL PURPOSES

(76) Inventor: Heribert Schmid, Kiefernstrasse 14, D-82194 Groebenzell (DE)

( * ) Notice: Subject to any disclaimer, the term of this patent is extended or adjusted under 35 U.S.C. 154(b) by 0 days.

(21) Appl. No.: 09/479,138

(22) Filed: Jan. 7, 2000

Related U.S. Application Data

(63) Continuation-in-part of application No. PCT/EP99/03174, filed on May 10, 1999.

(51) Int. Cl.[7] .................... A61C 1/00; A61C 1/18; A61C 1/06; A61B 17/14
(52) U.S. Cl. .................... 433/27; 433/131; 433/224
(58) Field of Search .................... 433/27, 102, 103, 433/131, 224; 73/116

(56) References Cited

U.S. PATENT DOCUMENTS

| | | | |
|---|---|---|---|
| 5,538,423 A | * | 7/1996 | Coss et al. ............ 433/27 |
| 5,543,695 A | * | 8/1996 | Culp et al. ............ 318/432 |
| 5,980,248 A | * | 11/1999 | Kusakabe et al. ...... 433/27 |
| 6,017,354 A | * | 1/2000 | Culp et al. ............ 606/170 |
| 6,090,123 A | * | 7/2000 | Culp et al. ............ 606/180 |

FOREIGN PATENT DOCUMENTS

| | | |
|---|---|---|
| DE | 196 28 854 A1 | 1/1997 |
| DE | 297 12 012 U1 | 1/1998 |
| EP | 0 812 578 A | 12/1997 |

* cited by examiner

Primary Examiner—Ralph A. Lewis
(74) Attorney, Agent, or Firm—Graybeal Jackson Haley LLP

(57) ABSTRACT

The invention concerns an electric drive device for medical applications, especially for driving drills, cutting instruments and screw drivers. Such endo-instruments have predetermined working rotation areas and comprise maximally permissible torque load limits according to the materials thereof. The drive device is equipped with a stepping motor in order to avoid exceeding the torque load limits. The stepping motor disconnects when the maximum torque limit of the stepping motor is fixed below the torque load limit of the instrument. In order to precisely set the torque load limit, a calibration is carried out within the limits of a no-load operation during which the efficiency of the driving shaft up to the instrument is detected, and with it, the value of the current is determined for a zero torque.

21 Claims, 4 Drawing Sheets

Figure 1:
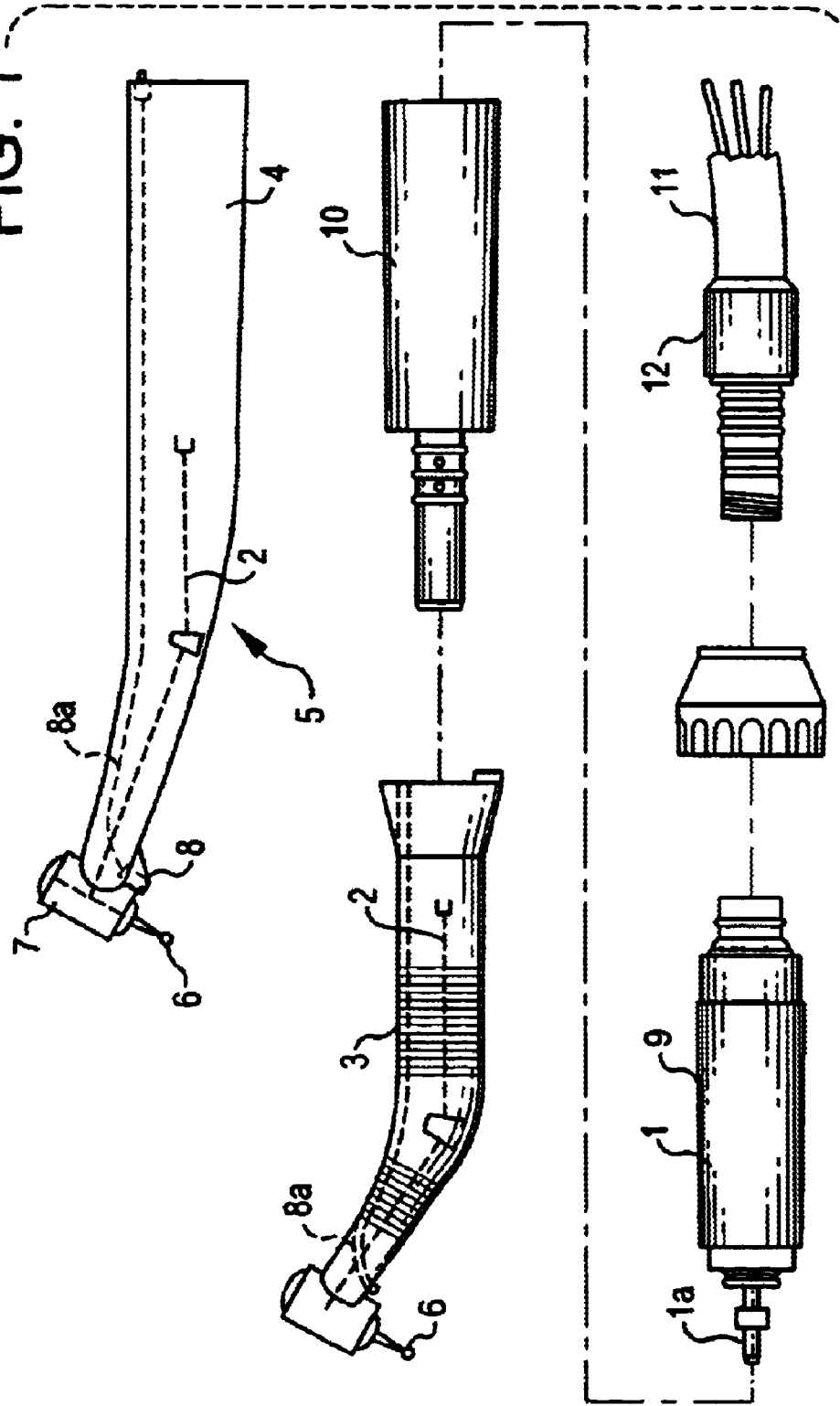

WORKING DEVICE FOR DRILLING, CUTTING AND SCREWDRIVER INSTRUMENTS USED FOR MEDICAL PURPOSES

This is a continuation-in-part of International Application PCT/EP99/03174 filed May 10, 1999, designating the United States.

DESCRIPTION

The present invention is concerned with an electrical drive mechanism for drills, cutting tool and screw drivers which are employed, customarily, for surgical purposes. The invention also concerns a process for the modulation of the drive mechanism and for the monitoring of the state of the driven tool.

In the field of medicine, operational apparatuses of this kind, are used especially in dentistry for common root canal preparatory work, and also for boring and cutting threads into bone structure, which would include borings for insertions such as rods. In addition, these operations are carried out manually by the dentist or an operator, in order to avoid damage to the teeth or to the bone being treated.

For instance, in dentistry, normal root canal preparations are carried out by means of an electrically driven drill, which is seated in a dental hand piece. Generally, a non-commutator, direct current drive is employed, such as is marketed by the firm KaVo under the designation "INTRAmatic LUX". This type of drive, which is usually dedicated for application in dental drilling operations, is driven, within the scope of dentally approved control in the lower range of 2000 to 4000 RPM up to, in the highest rotational speed range, about 4000 to 60,000 RPM and at a torque of 2 to 3 Ncm. These drive units are incorporated within the dental hand piece.

For root canal preparatory work, however, flexible endo-tools are used, by means of which root canals, which can exhibit varied diameters and different paths, are cleaned out. This is carried out, for instance, with a spiral shaped, flexible drill, tapering toward the point and of a length of approximately 20 to 30 mm. This device, by means of its turning, screws itself into the root canal, whereby, upon the withdrawal thereof, the canal is reamed out. According to the manufacturer of this kind of a drill, the rotation speed of the same runs in a range of about 100 to 500 RPM. In exceptional cases, this might be as high as 1800 RPM. Then, in order to achieve the optimal operative range for this tool, motors selected from those now available, must be inserted into the conventional hand piece. These motors, with the previously named speeds of rotation of 2000 to 4000 must possess in the drive train, a speed reducer of i=16:1 to 20:1. By means of drives of this kind, indeed the applicable area of known electric motors for surgical purposes has been extended to include the drives for spiral drill of the described, generic kind. However, the speed reducer brings into activity a torque increase of exactly the above said ratio, reduced by the efficiency loss of the drive.

Investigations by the inventor have provided the results, that with this torque, nearly all of the endo-tools being used at this time, for instance for root canal preparatory work, are stressed above their breaking threshold. For instance, it has been demonstrated, that flexible spiral drills for the cleaning of root canals may only be loaded up to a maximum of 0.2 Ncm. If this torque threshold be overstepped, the spiral drill can break off and remain implanted in the root canal being treated. Accidents of this type, in many cases, can only be alleviated by an operative measure.

Thus, in the face of this problem, the purpose of the invention is to create an electrical drive mechanism for surgical endo-tools, the speed of rotation and torque ranges of which are variably adjustable by equipment of minimal control technological complexity. Further the purpose includes that the electrical drive mechanism can be employed by nearly all of the existing endo-tools, especially for drilling and also for cutting threads and the engaging of rods therein.

The invention of the present patent is comprised accordingly in the design of an electrical drive mechanism for tools for surgical drilling, cutting and screw thread related functions, with, respectively, a predetermined range of speeds of rotation and a maximum allowable torque loading threshold. The mechanism further encompasses an electrical stepping motor, the maximum torque and RPM of which can be preset by the magnitude of the current and the frequency of the rotational field. Extensive experiments brought forth the result, that with a stepping motor as a drive for contemporary endo-tools, the breakage of said tools is prevented in their practical applications. In accomplishing this, one is making use of the effect of "falling out of step", which, when pushed to the highest degree, results in a blockage of the motor upon overload. The regulatory technical complexity remains at a minimal level and limits itself to the adjustment of the ampere load as well as the pulse generation for the stepping motor.

A particular goal of the invention is that the above described mechanism must be adaptable for different hand pieces and thus for different drive shaft appurtenances, which again, exhibit varying degrees of efficiency. Expressed in other words, the maximum torque generated by the motor in a hand piece does not match the maximum torque applied directly to the tool. The invented procedure for the corrective compensation of the drive mechanism provides a self-calibration step, which is carried out in operation following an exchange of the hand piece or hand grip carrying the drive train. This said step, however, can be executed also at designated time periods. Principally, in this matter, the invented stepping motor is loaded with a predetermined minimal electrical current below the initial start-up current level. Subsequently, the amperage is increased incrementally up to the point where the motor starts to run. This final amperage value, which activates a start of the stepping motor, is saved in memory as that current, which is required for overcoming the friction of the drive shaft train and which, as a result, is also proportional to the current consumed by the drive chain.

The electrical drive mechanism is thereby improved in that a drive shaft of the stepping motor is coupled to the tool with or without an up or down ratio transmission. Under these circumstances, the stepping motor again with/without an up or down transmission, possesses an operational rotational speed range of from 100 to 300 RPM and drops out of step upon a loading equal to, or greater than its adjusted preset torque.

The operational rotational speed range is also the start-stop-RPM spread of the stepping motor, within which the said motor, after dropping out of step, upon a lessening of the torque loading, can recover itself and start to run again. It is advantageous if the stepping motor, even outside of its said start-stop-RPM, can be run up to a rotational speed of 6000 RPM.

The above described development thus enables a more extensive use of an electrical drive with tools having a low fracturing load and brings about a substantial lessening of the danger of break-off of the tool. This also opens the possibility of multiple usages of the same tool. Furthermore, it has become evident, that for endo-tools, which are subjected to a continually increasing time of operation, the failure-point loading thresholds, determined by the inventor in the meantime, are subject to a corresponding change. Within the context of tests, a maximum operational time could be determined analytically for some endo-tools, within which the likelihood of breakage is held down and the cutting ability of the tool is sufficient. Upon exceeding these maximum usage periods, it is noted that breakage as a result of material fatigue is seen to increase and as well, a substantial deterioration of the cutting performance becomes evident.

Thus, to make full use of the ability to operate at full capacity as well as maintain the safety potential of the newly developed drive concept of the inventor, the most exact knowledge about the condition of the tool in use is necessary, in order to prevent a break-off in every case, not only as a result of an impractical overload, but also as a result of material fatigue.

In view, then, of the problems presented, it is technically advantageous to make available a new procedure for recognizing the condition of a surgical tool, in particular, of an endo-tool.

In keeping with the invention, a procedure for the monitoring of the condition of an endo-tool, which at least encompasses the following steps:
 a. the input to a computer of the previously determined, maximum allowable loading quantity, of a specific tool,
 b. the determination of a partial loading quantity resulting from an actual treatment and the addition of this said partial loading quantity to a total loading quantity specific to the tool condition, which total quantity results from previous treatments,
 c. a comparison of the maximum allowable loading quantity with the up-to-date total loading quantity and
 d. the emitting of a "Need to Exchange" signal, in case the entire total loading quantity reaches the loading threshold or exceeds the same.

By means of the foregoing, described procedure, there will be subsequently assigned to a tool, for instance, a flexible spiral drill, a maximum loading quantity for which the risk of break-off is minimal and on a continuing basis, the "Condition Now" loading quantity is computed and compared with the maximum loading quantity. In this manner, a sufficiently safe condition of the tool can be assured.

In accord with claim 15, the loading quantity is defined as a theoretical amount, which is defined by the running rotational RPM speed, the torque, and the length of the surgical treatment. Additionally, or alternately, the number of sterilization cycles can serve as a value to be compiled in the total loading quantity.

Additional advantageous embodiments of the invention are, in this matter, subjects of the subordinate claims.

The invention is, in the following, described in greater detail with the aid of a drawing of a preferred embodiment.

Figure 2:
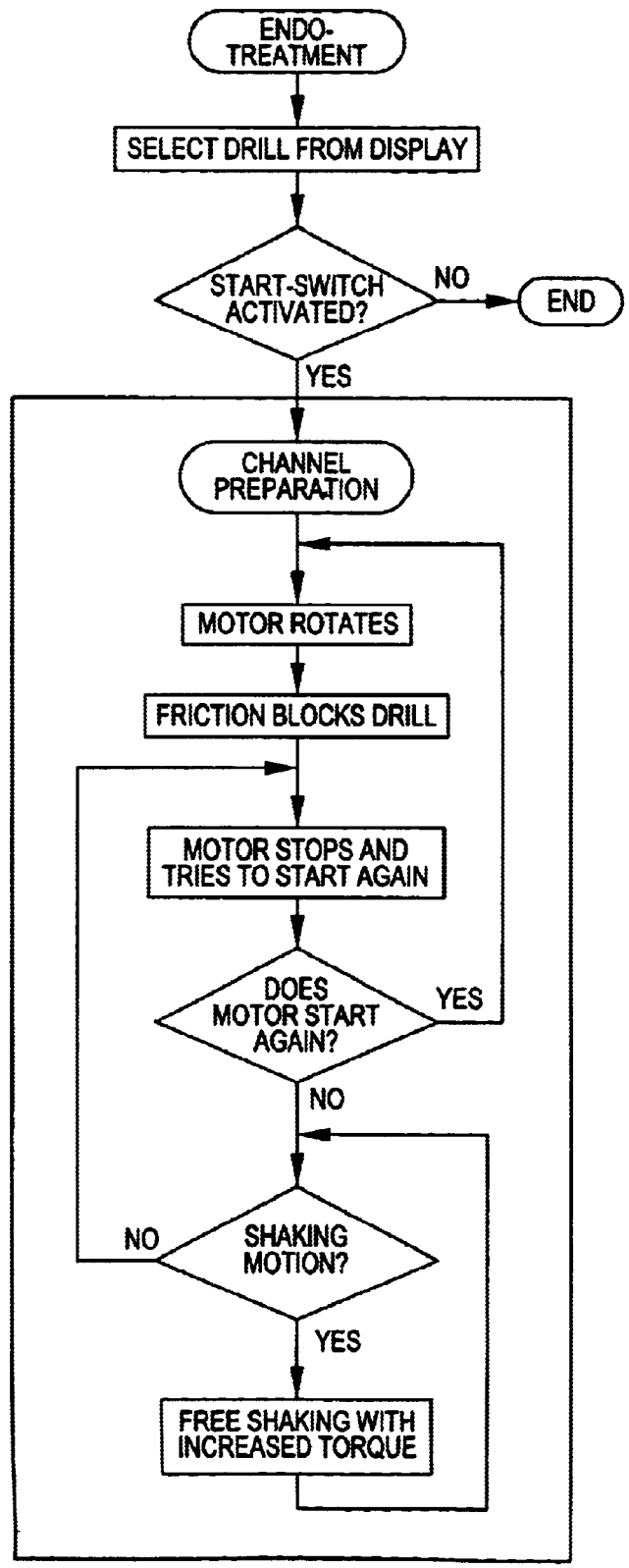
Figure 3:
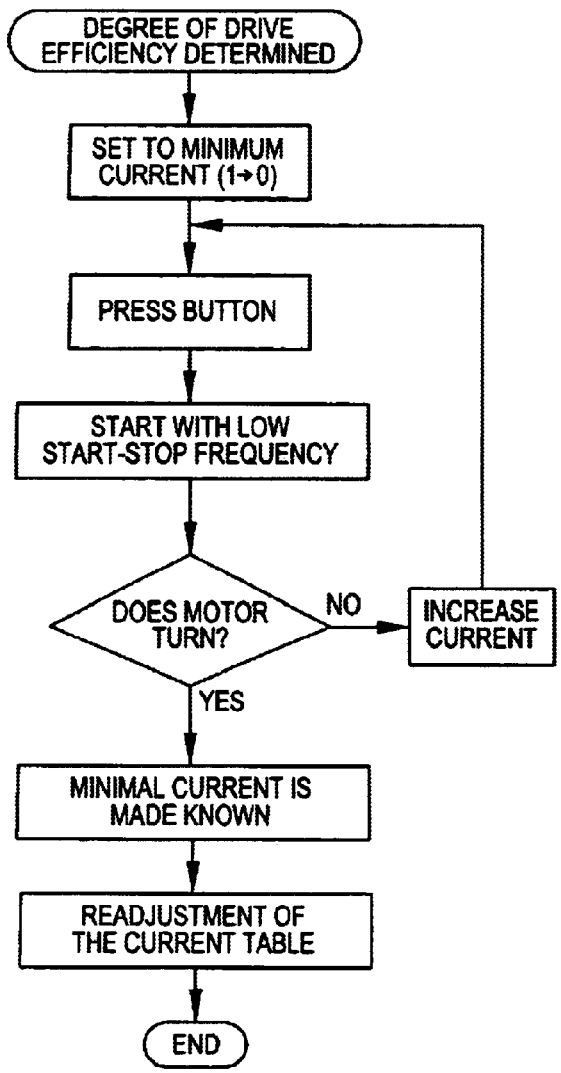
Figure 4:
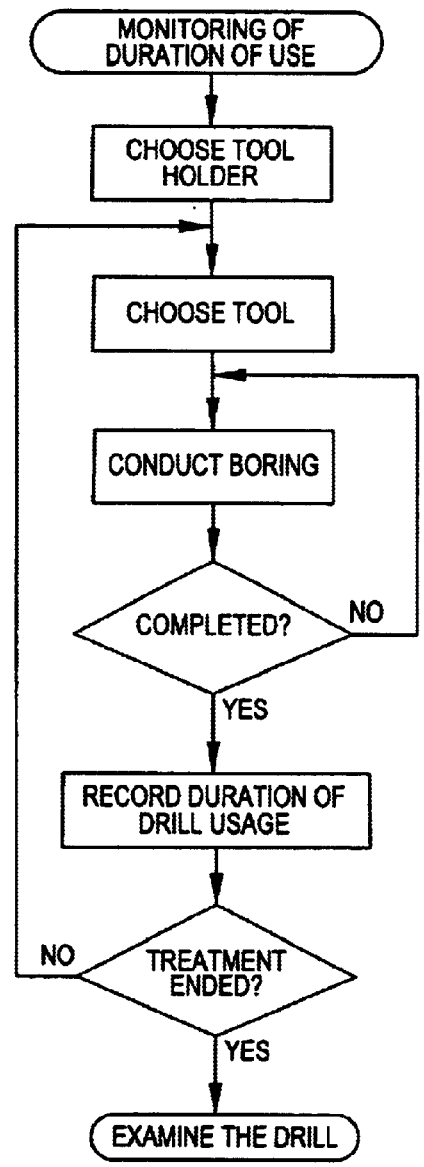
Figure 5:
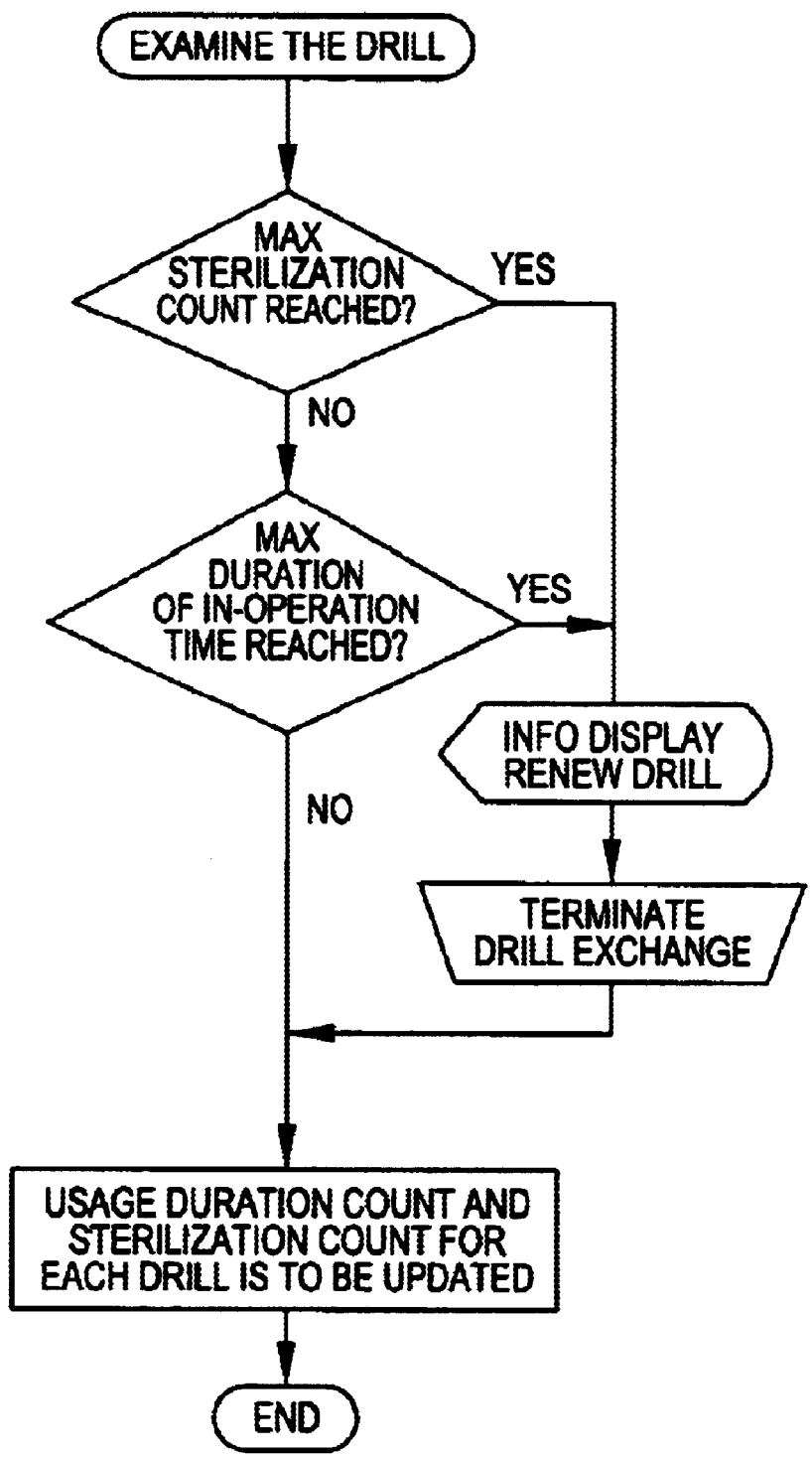

FIG. 1 shows as a possible application example of the invention the general construction of an angular piece universally used in dental practice for the seating of drills as well as for the installation of an electric motor, FIG. 2 shows a flow-diagram relative to an operational procedure in accord with the invention in the case of a root canal treatment, FIG. 3 shows a flow-diagram in regard to a self calibration process, FIG. 4 shows a flow-diagram in regard to the running course of a program for monitoring a time-of-usage duration in accord with a preferred embodiment of the invention and FIG. 5 shows a flow-diagram for the programmed sequence of the monitoring of a sterilization cycle in accord with the invention, using as example, a spiral drill.

As may be inferred from FIG. 1, the dental hand piece arrangement is comprised of an electric motor 1 onto the free shaft end 1a of which is coupled the drive shaft section 2 of a hand piece 5, which said hand piece exhibits a curved gripping sheath 3. On the outer end of hand piece 5 is a gripping sheath 3 on which a drill head 7 is placed. On the opposite front end is fastened an additional sheath 4, which encapsulates the drive motor 1. On the drill head 7, which accepts a rotatable tool, such as a drill 6, is also situated an illumination device 8 with a supply line 8a.

In accord with the invention, the drive motor 1 is designed as a stepping motor, which possesses the characteristics described in the following.

The stepping motor 1 has an operating rotational speed of 0 to 6000 RPM and about 100 to 300 RPM within the frequency of the start-stop-RPM band, wherein the torque range thereof lies between 0 and about 4 Ncm. The stepping motor 1 is comprised of a rotor (not shown) with power take-off shaft 1a and a stator (not shown), both enclosed by an outer casing 9 thus building a "motor cartridge", which is inserted into a jacket shaped adapter cartridge 10, which, in turn, is axially pushed into the hand piece part, that is, into the additional sheath 4 which is fastened to the forward end of the gripping sheath 3. The cartridge 10 is also affixed within the said sheath 3. The connection between the stepping motor 1 and the supply cable 11, can be made in various ways.

As is further presented in FIG. 1, the power take-off shaft 1a of the stepping motor 1 is directly coupled with the drive shaft section 2 serving the tool 6 without any high or low ratio transmission gearing. That is, the drive shaft section 2 rotates at the same RPM as the take-off shaft 1a of the stepping motor 1. Naturally, a high or low ratio transmission can be installed in the curved gripping sheath 3. Also, the electrical drive mechanism 1, upon an exchange of gripping sheath 3, can be optionally equipped with a low/high ratio transmission or even without any transmission simply by plugging the present gripping sheath 3 onto the adapter cartridge 10.

Numerous trials for the ability to withstand loadings were previously conducted on the endo-tool, which is to be driven by the electrical mechanism. This basis contributed to the development of the electrical drive mechanism, which in accord with the invention, incorporates:
 the stepping motor with a rotational speed of 0 to 6000 RPM and a torque between 0 and 4 Ncm,
 the power take-off shaft 1a of the stepping motor 1, and
 the drive shaft section 2.

These trials will be briefly described further in the following.

First, experiments were run with flexible endo-tools applicable for dental purposes, in particular regarding root canal preparations. As already briefly discussed in the introductory passages, these endo-tools are designed as flexible, spiral shaped drills, which taper toward the tip and preferably are made of nickel-titanium alloy. The maximum allowable rotational speed of drills of this kind is about 100 to 1800 RPM. The experiments demonstrated, that fine drills of this generic type fracture upon a torque of about 0.2 Ncm. Further, upon overstepping this torque threshold, the break occurs at the extreme tip end of the drill. Additional practical experiments with the known electrical drive mechanisms for powering the aforesaid, specific drill have shown, that the already determined limit of 0.2 Ncm is being overstepped. In practice, root canals do not run in a straight line, but are curved, kinked and exhibit different depths. To this extent, the heightened danger exists, that the drill is likely to fracture upon reaching one of these kinks with the root canal or upon reaching the end of said canal. This occurs because the electrical drive mechanism possesses a drive moment which is too high. This happens so quickly and surprisingly, that the operating doctor has no possible means of avoidance, for instance, of shutting off the drill by an instant switching off or withdrawal of the electrical drive mechanism.

The invented electrical drive mechanism, however, in accord with foregoing commentary, employs the stepping motor 1 and makes use of the characteristics of a stepping motor for an operational procedure as per FIG. 2, for instance for a root canal treatment, as follows:

The employed stepping motor 1 operates within a rotational speed range of 100 and 300 RPM within its start-stop-RPM band. That is, if the motor is loaded above its preset, maximum torque, it fallso of step but still attempts, on its own, to run again. However, it cannot resume operation until the torque demand has diminished. This "falling-out-of-step" is not only audible, but unmistakably detectable by the treating doctor due to the vibration of the hand piece.

This "falling-out-of-step" of the motor prevents an overloading of the stepping motor and does this within the time span between the start of the overload and the recognition thereof, i.e. reaction, by the treating doctor. This is to say, that an overload of the spiral drill beyond the set maximum torque limit is avoided, so that in any case, a break as a result of a torque overload is prevented.

Further, the direct drive of the tool by the drive mechanism without a low/high ratio transmission enables an essentially exact setting of the maximum achievable torque on the tool by means of determining the maximum allowable input amperage as well as the permissible rotational speed of the stepping motor. Under these circumstances, it is possible, in the case of the invented stepping motor, to not only exactly set the RPM and torque, but also the direction of rotation, whereby the following function is enabled:

Under the assumption, that in the course of cleaning out a root canal the drill has frozen itself in the tissue, and consequently the drive mechanism, as a result of the attendant high torque, has fallen out of step, then, the stepping motor attempts, within the start-stop-RPM band, to restore its operation. This leads to a vibration or shaking motion, which the operating doctor feels at the handgrip. Now the possibility arises, to so control the stepping motor (i.e. the rotating field frequency whereof is presented in FIG. 2), that the motor changes the direction of rotation in an alternating manner, generating a planned, definite back and forth motion, for instance, a so-called Pilgrim step, in the case of which a turn forward is always greater than the subsequential backwards turn. In other words, the back and forth turning is accompanied with an increasing application of current, but which is proportional to that torque, which lies under the maximum allowable torque, and carries this on, until the drill has wrenched itself free. When the drill is free, the turning then continues in the original direction. This reinforcing mode can be done either manually by the attending doctor or automatically introduced upon an overstep of the maximum torque.

Evidence has been given, that such tools as are operated at a higher rotational speed, that is, at 2000 RPM, can also be driven by means of the invented electrical drive mechanism, that is, outside of the start-stop-RPM. The invented stepping motor, in such a case, can be accelerated through a defined speed increase curve, whereupon it falls out of step, that is, it remains immovable, when the torque to which the stepping motor is subjected exceeds its set maximal torque limit. If the invented stepping motor be driven in this rotational speed range of 2000 RPM, then, the stepping motor cannot, of itself, resume operation when it drops out of step,. In order to bring the motor up to an allowable RPM again, the rotating field frequency must be dropped manually to less than its corresponding start-stop-RPM, for instance by means of a foot switch. When this is done, the motor can again be driven up to the required operational speed of the tool in use.

From the above description of the invented electrical driving mechanism, it becomes obvious that this can be applied to numerous other surgical purposes. Since the rotational speed as well as the torque can be easily and exactly input to the stepping motor, and thereby also the RPM as well as the maximal torque can be controllably set for the tool itself, the cutting of threads in prebored openings can be done, as this may be called for in bone surgery. The threading presents no problem, since by an overload of the motor in accord with its maximal torque threshold, the motor simply remains in still-stand, and only makes an effort to resume running again. Also, where the invented stepping motor is concerned, the possibility exists that the direction of rotation can be reversed in a very simple manner. Thus either the drill or thread cutter, after a specified travel, that is, penetration depth, can be precisely withdrawn again. The same is valid, naturally for the screwing of threaded rods into the said threaded borings.

As an additional apparatus for the invented operational mechanism, an electrical switchboard can be provided, allowing storage of a multiplicity of different tool types as well as memory for technical data. In this way, the operating doctor need only input or call up the tool type to be used, in order adjust the operating apparatus to the admissible values of the respective tool.

As additional fields of application, the following are described:

1. In a case of caries treatment, use was made of the fact, that tooth enamel which has been subjected to caries possesses a lesser hardness than does healthy tooth enamel. That is, ailing tooth areas alter their structure and therewith lessen their structural strength and hardness as compared to healthy tooth areas. The stepping motor can now be so adjusted, that the maximum developed torque suffices to drive a drill in the softer tooth material, in order to clear this out. However, as soon as the drill hits upon the healthy tooth enamel, the torque to which the drill is subjected oversteps this maximum torque limit, whereupon the stepping motor stops. The more healthy tooth enamel thus remains nearly totally in its original condition. Furthermore, a drill operated in this manner generates a small warning vibration, which in the case of the removal of healthy enamel would be magnified, whereby during the treatment, there is a reduction in pain caused by traumatizing, that is, by a contraction of the nerve chamber.

2. The same applies also in the case of the removal of tartar deposits, which, as compared to tooth enamel, possess likewise other characterizations in regard to hardness and structural strength, for which the invented drive mechanism can be adjusted in regard to RPM and torque limits.

As was briefly mentioned at the beginning of this description, the invented drive mechanism should be as flexible as possible in regard to extent of application (different surgical usage possibilities) as well as likewise flexible where different hand piece construction is concerned. In the framework of the multiple trials, it has been shown, that in spite of exact, adjustable RPMs and torques acting upon the stepping motor itself, variations, that is RPM deviations and torque irregularities, do directly affect the tool when used in different hand pieces.

The grounds for this are comprised, in that special angular hand pieces with varied bending angles, materials, drive shaft appurtenances, bearings and the like, possess different efficiencies. Briefly stated, this means that hand pieces of different manufacturers deviate from one another in said efficiency and design. That means, that if a specified torque were preset in an invented stepping motor, then, the actual maximum torque reaching the drill is lessened, in correspondence to the degree of efficiency (torque loss, for instance by friction) which corresponds in turn to the employed hand piece.

The result of this is, that an exact adjustment of the torque at the tool is practically impossible.

The solution to this problem exists in the self calibrating ability process of the invention as this is presented in FIG. 3.

At each start of the operation of the drive mechanism and/or at a preset time interval by the operating doctor or yet after a change of the grip piece, in accord with FIG. 3, there is introduced for a given drive, a self calibration procedure in the form of a designed dry-run program,—that is, drive shaft traction determination. This program is initiated by means of the activation of a "Calibration Button" (not further described), whereupon, the stepping motor is loaded in a first program step with a minimal electrical current. This minimal current is selected to be less than the stepping motor's own start amperage or is already circuitously pre-installed at said insufficient amperage, so that the motor, upon application of said current does not start.

Following a definite number of controlled rotating field sequences, the electric current is increased by specified increments until the stepping motor does start. This start-up of the stepping motor is detected either visually or acoustically by the doctor or picked up by a sensor, whereupon the self-calibration process, described in FIG. 3 with the current increase program loop, is manually or automatically ended. Upon the termination of this program loop, the program proceeds to the next step, in which the last adjusted electrical current is saved as a start-up current in a table. This same start-up (or break-away) current represents simultaneously the value of the lost current through the angular grip piece in use and is, indirectly, a value for the system efficiency.

If now the desired current strength in accord with the tool to be used, or the current for the intended kind of treatment is input by the doctor, the computer which executes the program adds the previously measured loss current to the input value in order to compensate for the expected loss through the angular gripping piece or a possible subsequent drive train. In this manner, the maximum torque at the tool represents very exactly, the input current value.

The aforesaid described self-calibration can also be factory installed by the manufacturer of the angular hand piece as a standard function and in the form of an electrical code, which is legible for reading or manually input into the computer with reading means on the housing of the angular hand-piece. That is, angle piece, hand piece, drive shaft traction, etc. are already factory provided with a degree of efficiency statement. The doctor can given consideration to this upon input of the maximum allowable current value or, as an alternative, be informed thereof by the computer. To have this information, the computer would then require receipt of a signal from an appropriate sensor. The information provided thereby, would be used as loss current in correction of the manually input current table.

Accordingly, the invention concerns an electrical drive mechanism for surgical applications, especially for the drive of drills, cutting tools, and screw related tools. Endo-tools of this kind have predetermined operational speeds of rotation ranges and possess torque loading limits. In order to avoid exceeding these individual torque loading limits, the drive mechanism is equipped with a stepping motor. Upon reaching its maximum torque limit, the said stepping motor falls out of step, wherein the maximum torque of the stepping motor is set to be less than the torque threshold of the driven tool. In order to be able to set the torque loading limit exactly, the drive mechanism runs a self-calibration program within the framework of a dry run, in which the efficiency up to the tool of the drive shaft currently in use is determined, and thereby the amperage for a zero point torque is determined.

For the following description of a program for the monitoring of the up-to-the-minute condition [of the tool], be advised that a type of storage magazine for different tools in the form of a number of holders or boxes has been prepared, in which the tools are stored, each being numbered or otherwise coded.

A computer (not described), which already contains input with the quantity of the individual tools, the location, and/or the kind of the said individual tool, manages this tool holder and assigns to each tool therein a value specific to its present condition, as will be described in the following.

The time-of-use monitoring program, in accord with FIG. 4, can be initiated either manually before the beginning of a treatment or automatically at each start-up of an electrical drive mechanism, in this case especially the start of a stepping motor, which has been put into use for a root canal treatment.

At the beginning, the dentist conducting the treatment selects from the magazine a holder, preferably filled with only one kind of tools, which are particularly suited for the intended treatment. The doctor removes one of these tools from said holder. Subsequently the doctor inputs the code of this tool into the computer. Alternative to this, the computer can be equipped with a suitable sensor device, which enables the computer to be provided with an automatic readout and recognition of the chosen tool.

As has been already indicated in the introductory passages, for each tool—especially where dental operations are concerned—there is to be analytically determined special values, namely rotational speed, loading, total length of service in the life of the tool, and a maximum number of sterilization cycles. From these values a maximum loading value can be determined as a theoretical quantity, wherein, by the exceeding of the same, a substantial increase in the probable breakage by fatigue is determined. This maximum allowable value, that is, the maximum loading quantity, is input into the computer for each tool to be found in the said magazine. This input for sorting out is made either manually or automatically per sensor response. Now the computer is in a position to display the characteristics specific to a given tool when the corresponding code call-up is made.

After the tool, this being, for instance, a flexible spiral drill used for a root canal preparation, is inserted into the hand piece, and the computer is informed as to the tool-in-use, the doctor/dentist can begin the treatment, in which the drive mechanism is started up. Upon the starting up of the of the drive mechanism, the computer measures continuously the duration of operational time, the amperage to be used as a base value for computing the degree of loading, and it records the RPM and/or in case of a stepping motor the number of pulses as a reference base of complete revolutions and saves these values as values specific to the tool condition in an intermediate memory.

At the completion of the treatment, the doctor switches off the drive mechanism or, alternatively, gives a "shut-down" signal to the computer in order to provide said computer with a signal that the treatment time for this tool has come to an end. The computer now evaluates the measured and saved values specific to tool condition, which present a loading profile for the now-completed treatment and computes from these data, a theoretical partial loading quantity. The partial loading quantity now becomes a total loading quantity by incorporating previous treatment time (if any) using the same tool. In this way, the life loading values for this tool has been brought up to date. At this point, the program ends itself.

After the termination of the foregoing described program run-out, the computer undertakes a sterilization cycle monitoring program.

The tool used by the doctor, after the treatment, is returned to the said tool holder. The tool holder and the tool are subsequently cleaned and subjected to a sterilization process. Trials have shown, that this sterilization process attacks the tool and leads to an accelerated alteration of material, particularly in the dulling of the said tool. On these grounds after each treatment, the computer counts the number of the sterilization cycles, in order to compile the life total of sterilization cycles for this just employed tool.

After the compilation of the true values specific to the tool, including the lifetime total of sterilization cycles and the total loading quantities, the computer then compares, in accord with FIG. 5, this present as-is-value with the maximum allowable values specific for the tool just employed, and furnishes a warning signal upon reaching or overstepping of one of the maximum threshold values. This could warn the doctor as to the necessary replacement of the tool in question. In this case, the doctor would not again store the tool in the holder, but replace with a new tool.

As may be inferred from the foregoing description, in this particular embodiment, only after the ending of a treatment is the as-is-condition of the tool declared and compared with the maximum allowable condition. However, the case can come up, that during the a treatment, for instance the maximum in-use duration, that is, the predetermined maximum total loading quantity, is reached or even exceeded. In order to solve this problem in the most simple manner, in accord with the preceding embodiment, upon the determination of the maximum total loading quantity, a safety factor is computed, which is so chosen, that within the framework of an average treatment, with the corresponding tool, this actual maximum loading factor cannot be reached.

Alternative to this simple mode of procedure, the course of the program run-out can be altered in such a fashion, that an addition program loop, perhaps called, "Determination of the tool condition and comparison of the as-is-condition with the maximum total loading quantity" can be interposed before the step shown in FIG. 4, entitled "Examine the drill", so that a corresponding warning signal, if necessary, can be displayed to the doctor even during the treatment. In this case, the safety factor for each tool could be reduced and the duration period for the said tool be prolonged.

What is claimed is:

1. An electrical drive mechanism for tools for surgical drilling, cutting and screwing related activities with respectively a predetermined rotational speed range and a maximum allowable torque loading threshold, the drive mechanism comprising:

an electric stepping motor operable to rotate a tool at a torque, wherein the torque and the rotational speed of the tool are preset respectively by fixed values of the magnitude of the current and the frequency of the rotating field received by the motor, and wherein, when the tool encounters a load, the magnitude of the current and the frequency of the rotating field remain at their preset values; and a means for monitoring and modifying the magnitude of the current.

2. An electrical drive mechanism in accord with claim 1, further comprising, a power take-off shaft at an end of the stepping motor coupled to a tool.

3. An electrical drive mechanism in accord with claim 1 wherein the stepping motor possesses an operating rotational speed range of 100 to 300 RPM and falls out of step upon being subjected to a torque load equal to, or greater than, its preset torque load limit.

4. An electrical drive mechanism in accord with claim 3 wherein after the stepping motor falls out of step, the stepping motor is operable to repeatedly alternate the direction of rotation with an increasing supply of current to overcome a condition causing the stepping motor to fall out of step then resume rotation in its original direction, and wherein the magnitude of the supply of current does not exceed the preset value associated with the torque.

5. The electrical drive mechanism in accord with claim 4 wherein the repeating alternating directional rotation is limited to a predetermined number of degrees.

6. An electrical drive mechanism in accord with claim 1 wherein the operational rotational speed range is in the start-stop-RPM band of the stepping motor and after falling out of step can resume running after a reduction of the torque load.

7. An electrical drive mechanism in accord with claim 1 wherein the stepping motor, operating outside of the start-stop-RPM band, is operable up to a speed of 6000 RPM.

8. An electrical drive mechanism in accord with claim 1 wherein the stepping motor develops torque between 0 and 4 Ncm.

9. An electrical drive mechanism in accord with claim 1 wherein the electrical drive mechanism is a dental hand piece having an angled shape and further having a drive shaft train therein; and wherein the stepping motor is adapted to power the drive shaft train.

10. The electrical drive mechanism of claim 1 wherein the means for monitoring and modifying the magnitude of the current comprises a self calibration program means comprising:

a means for supplying a stepping motor with a current below that of start-up current specific to the stepping motor;

a means for increasing incrementally the current supplied to the stepping motor; and a means for capturing the value of the current at which the stepping motor starts.

11. The electrical drive mechanism of claim 10 wherein the self calibration program means further comprises:

a means for storing the captured current value in a memory; and a means for adding the stored captured current value to an existing stored maximum current value.

12. The electrical drive mechanism of claim 10 wherein the self calibration program means further comprises a means for carrying out the self calibration program means upon initiation of operation of the electrical drive mechanism.

a means for adjusting a start-up current specific to a stepping motor in accordance with the value of the loss current for the hand piece.

13. The electrical drive mechanism of claim 10 wherein the self calibration program means further comprises a means for carrying out the self calibration program means upon exchange of a hand piece.

14. The electrical drive mechanism of claim 10 wherein the self calibration program means further comprises a means for carrying out the self calibration program means in accordance with a preset time period.

15. The electrical drive mechanism of claim 10 wherein the self calibration program means further comprises a means for carrying out the self calibration program means in accordance with a selectable time period.

16. The electrical drive mechanism of claim 1 wherein the means for monitoring and modifying the magnitude of the current comprises a calibration program means comprising:

a means for receiving into a memory a factory provided loss current for a hand piece;

17. The electrical drive mechanism of claim 1 wherein the means for monitoring and modifying the magnitude of the current comprises an as-is condition evaluation program means comprising:

a means for receiving into a computer a maximum allowable loading quantity;

a means for capturing a partial loading quantity for a treatment;

a means for adding the partial loading quantity to a compiled loading quantity from previous treatments to arrive at a total loading quantity;

a means for comparing the total loading quantity to the maximum allowable loading quantity; and a means for providing a warning signal if the maximum allowable loading quantity has been met or exceeded by the total loading quantity.

18. The electrical drive mechanism of claim 17, wherein the as-is condition evaluation program means further comprises:

a means for determining the maximum loading quantity from RPM, torque and length of treatment data.

19. The electrical drive mechanism of claim 17 wherein the as-is condition evaluation program means further comprises:

a means for assigning to a tool in a tool holder a value representative of its total loading quantity.

20. The electrical drive mechanism of claim 17 wherein the as-is condition evaluation program means further comprises:

a means for determining life total sterilization cycles of the tool;

a means for comparing life total sterilization cycles with a maximum sterilization count; and a means for providing a warning signal if the maximum sterilization count has been reached.

21. The electrical drive mechanism of claim 17 wherein the as-is condition evaluation program means further comprises:

a means for adjusting the total loading quantity associated with a tool upon replacement of the tool.

* * * * *

UNITED STATES PATENT AND TRADEMARK OFFICE
CERTIFICATE OF CORRECTION

PATENT NO.     : 6,616,446 B1
DATED          : September 9, 2003
INVENTOR(S)    : Schmid It is certified that error appears in the above-identified patent and that said Letters Patent is hereby corrected as shown below:

<u>Column 11,</u>
Line 6, please delete "a means for adjusting a start-up current specific to a stepping motor in accordance with the value of the loss current for the hand piece."
Between lines 25 and 26, please insert -- a means for adjusting a start-up current specific to a stepping motor in accordance with the value of the loss current for the hand piece. --

Signed and Sealed this

Twenty-third Day of December, 2003

JAMES E. ROGAN
*Director of the United States Patent and Trademark Office*